(12) United States Patent
Sexton

(10) Patent No.: US 10,901,980 B2
(45) Date of Patent: Jan. 26, 2021

(54) HEALTH CARE CLINICAL DATA CONTROLLED DATA SET GENERATOR

(71) Applicant: International Business Machines Corporation, Armonk, NY (US)

(72) Inventor: James A. Sexton, Plano, TX (US)

(73) Assignee: International Business Machines Corporation, Armonk, NY (US)

(*) Notice: Subject to any disclaimer, the term of this patent is extended or adjusted under 35 U.S.C. 154(b) by 142 days.

(21) Appl. No.: 16/174,639

(22) Filed: Oct. 30, 2018

(65) Prior Publication Data

US 2020/0134063 A1    Apr. 30, 2020

(51) Int. Cl.
*G16H 10/60* (2018.01)
*G06F 21/62* (2013.01)
*G06F 16/2458* (2019.01)
*G06F 16/23* (2019.01)

(52) U.S. Cl.
CPC ...... *G06F 16/2365* (2019.01); *G06F 16/2465* (2019.01); *G06F 21/6254* (2013.01); *G16H 10/60* (2018.01)

(58) Field of Classification Search
CPC ............ G06F 16/2365; G06F 16/2465; G06F 21/6254; G16H 10/60
See application file for complete search history.

(56) References Cited

U.S. PATENT DOCUMENTS

| 9,489,433 B2 | 11/2016 | Handler et al. |
| 2013/0132108 A1 | 5/2013 | Solilov et al. |
| 2015/0370992 A1 | 12/2015 | Yao et al. |
| 2016/0085931 A1* | 3/2016 | Cox ............ G06Q 50/24 705/3 |

OTHER PUBLICATIONS

Huang et al., "Knowledge-based patient data generation," Process Support and Knowledge Representation in Health Care: AIME 2013 Joint Workshop, KR4HC 2013/ProHealth 2013, Murcia, Spain, Jun. 1, 2013. (Year: 2013).*

(Continued)

*Primary Examiner* — Jay A Morrison
(74) *Attorney, Agent, or Firm* — Stephen R. Tkacs; Stephen J. Walder, Jr.; Reza Sarbakhsh

(57) ABSTRACT

A mechanism is provided in a data processing system comprising a processor and a memory, the memory comprising instructions that are executed by the processor to specifically configure the processor to implement a data set generator. A statistics gathering engine executing within the data set generator calculates statistics and metrics across multiple data dimensions for a plurality of clients and a plurality of each client's data sources. The statistics gathering engine stores the statistics and metrics in a client-specific data map data structure for each client. An aggregated data map engine executing within the data set generator aggregates the statistics and metrics into an aggregated data map. The aggregated data map engine stores the aggregated data map in an aggregated data map data structure. The data set generator creates a client database construct. An insert engine executing within the data set generator populates the client database construct with new data based on the aggregated data map data structure.

20 Claims, 10 Drawing Sheets

(56) References Cited

OTHER PUBLICATIONS

McLachlan et al., "Using the caremap with health incidents statistics for generating the realistic synthetic electronic healthcare record," 2016 IEEE International Conference on Healthcare Informatics (ICHI), IEEE, 2016. (Year: 2016).*

Aggarwal, Chard C. et al., "A General Survey of Privacy-Preserving Data Mining Models and Algorithms", http://www.charuaggarwal.net/generalsurvey.pdf, Oct. 2008, 42 pages.

Ali, Rahman et al., "GUDM: Automatic Generation of Unified Datasets for Learning and Reasoning in Healthcare", Sensors 2015, 15, 15772-15798; Jul. 2, 2015, 27 pages.

Anonymously, "System and Method for Generating Synthetic Dataset with Realistic Data Distribution for", IP.com No. IPCOM000243740D, IP.com Electronic Publication Date: Oct. 16, 2015, 10 pages.

Anonymously, "System and Method for the Automatic Generation of Models of Clinical Guidelines in Healthcare", IP.com No. IPCOM000239211D, IP.com Electronic Publication Date: Oct. 21, 2014, 5 pages.

Buczak, Anna L. et al., "Data-driven approach for creating synthetic electronic medical records", BMC Medical Informatics and Decision Making, Oct. 2010, vol. 10, No. 1, 28 pages.

Choi, Edward et al., "Generating Multi-label Discrete Patient Records using Generative Adversarial Networks", http://arxiv:1703.96490v3 ; Jan. 11, 2018, 20 pages.

High, Rob, "The Era of Cognitive Systems: An Inside Look at IBM Watson and How it Works", IBM Corporation, Redbooks, Dec. 12, 2012, 16 pages.

Slavov, Vasil et al., "A new tool for sharing and querying of clinical documents modeled using HL7 Version 3 standard", Journal of Computer Methods and Programs in Biomedicine archive vol. 112 Issue 3, Dec. 2013, 24 pages.

Walonoski, Jason A. et al., "Synthea: An approach, method and software mechanism for generating synthetic patients and the synthetic electronic health care record";, Oxford University Press on behalf of the American Medical Informatics Association, Journal of the American Medical Information Association, Sep. 2017, 10 pages.

Yuan, Michael J., "Watson and healthcare, How natural language processing and semantic search could revolutionize clinical decision support", IBM Corporation, IBM developerWorks, http://www.ibm.com/developerworks/industry/library/ind-watsont, Apr. 12, 2011, 14 pages.

* cited by examiner

HEALTH CARE CLINICAL DATA CONTROLLED DATA SET GENERATOR

BACKGROUND

The present application relates generally to an improved data processing apparatus and method and more specifically to mechanisms for generating a health care clinical data controlled data set.

An electronic health record (EHR) or electronic medical record (EMR) is the systematized collection of patient and population electronically-stored health information in a digital format. These records can be shared across different health care settings. Records are shared through network-connected, enterprise-wide information systems or other information networks and exchanges. EMRs may include a range of data, including demographics, medical history, medication and allergies, immunization status, laboratory test results, radiology images, vital signs, personal statistics like age and weight, and billing information.

EMR systems are designed to store data accurately and to capture the state of a patient across time. It eliminates the need to track down a patient's previous paper medical records and assists in ensuring data is accurate and legible. Due to the digital information being searchable and in a single file, EMRs are more effective when extracting medical data for the examination of possible trends and long term changes in a patient. Population-based studies of medical records may also be facilitated by the widespread adoption of EMRs.

Like any number of industries, healthcare is being transformed by the explosion of low-cost data. In healthcare, the transformation is driven in large part by EMR adoption and digitization. There have been many benefits. End users can take advantage of quantities of newly available information to solve problems in population health, clinical decision support, and patient engagement, among other applications.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to specifically configure the processor to implement a data set generator. The method comprises calculating, by a statistics gathering engine executing within the data set generator, statistics and metrics across multiple data dimensions for a plurality of clients and a plurality of each client's data sources and storing, by the statistics gathering engine, the statistics and metrics in a client-specific data map data structure for each client. The method further comprises aggregating, by an aggregated data map engine executing within the data set generator, the statistics and metrics into an aggregated data map and storing, by the aggregated data map engine, the aggregated data map in an aggregated data map data structure. The method further comprises creating, by the data set generator, a client contract database construct and populating, by an insert engine executing within the data set generator, the client contract database construct with new data based on the aggregated data map data structure.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
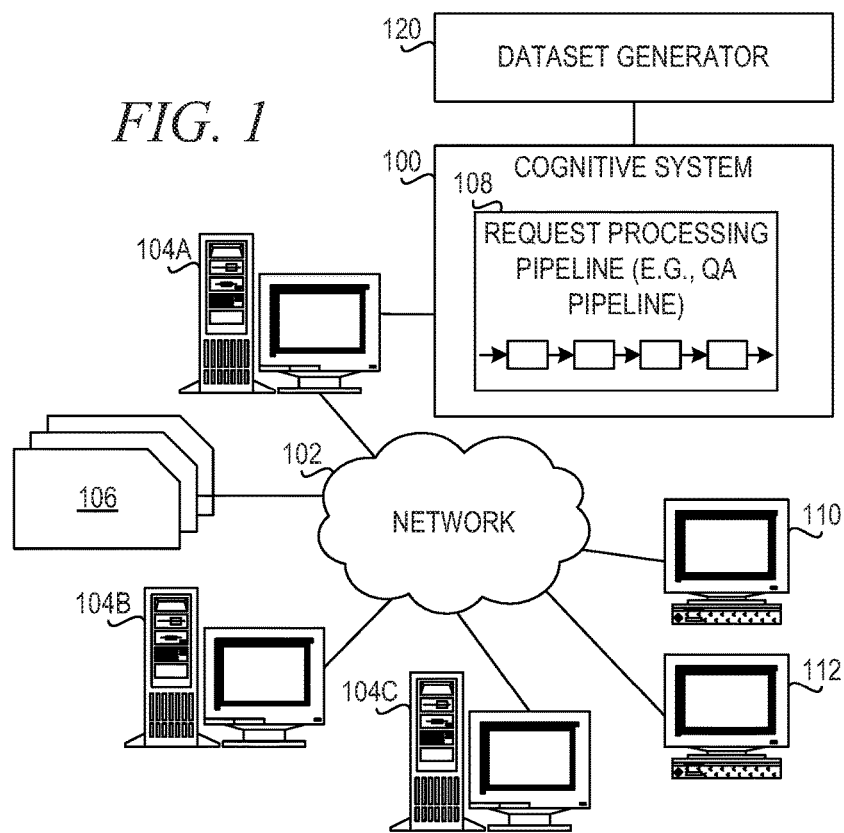
FIG. 1 depicts a schematic diagram of one illustrative embodiment of a cognitive healthcare system in a computer network.

Developing software for the healthcare industry involves developing software that ensures data security and complies with ever-changing regulations. The software developers must write software either by using fake data that mimics real patient data or by using real patient data. It is often very difficult contractually to get access to real patient data due to privacy concerns.

There are two major problems with respect to developing and testing against client data: 1) a single client's dataset does not contain a broad enough cross-section of data variability, and 2) client data is not controlled; therefore, expected results for validation vary depending on the state of the data. This variation worsens as the dataset ages. There are multiple disciplines that need different elements from the data. Due to the incredibly varied and chaotic nature of patient data, client health care data is messy. Additionally, the ever-changing state of data as it ages makes determining expected results of processing the data become less reliable each day. With as many different source systems from which data are obtained, and with as many varied ways that data are provided, the development and validation of health care data processing occurs by restoring a client's database from production, de-identifying it, and using the data available just in that database. Constructing a controlled dataset that merely meets the requirements of each individual discipline ignores the reality of client data. Additionally, restoring and using client databases for developing and testing only covers the data inclusive to that single client dataset.

Merely de-identifying data may not be sufficient. There are many instances where one can narrow down to whom data belongs using de-identified data. The illustrative embodiments provide mechanisms for generating artificial data that looks like real-life data. The illustrative embodiments capture and store some relevant statistics and value properties about a client's clinical dataset. The mechanisms of the illustrative embodiments are directed to capture and store these statistics from multiple client datasets in order to include data types, data states, and data values that are unique to an individual client dataset or specific to data from a particular data source, e.g., electronic medical records (EMR), practice management software (PMS), etc. The mechanisms of the illustrative embodiments then apply aggregation algorithms to determine a dataset that includes those data that are unique and those data that are aggregated, and the mechanisms load the results into a single aggregated data map data structure. The mechanisms of the illustrative embodiments include a module that can be directed to create an empty client dataset construct and then populate it with new data that retains the statistics and value properties of the aggregated data map.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
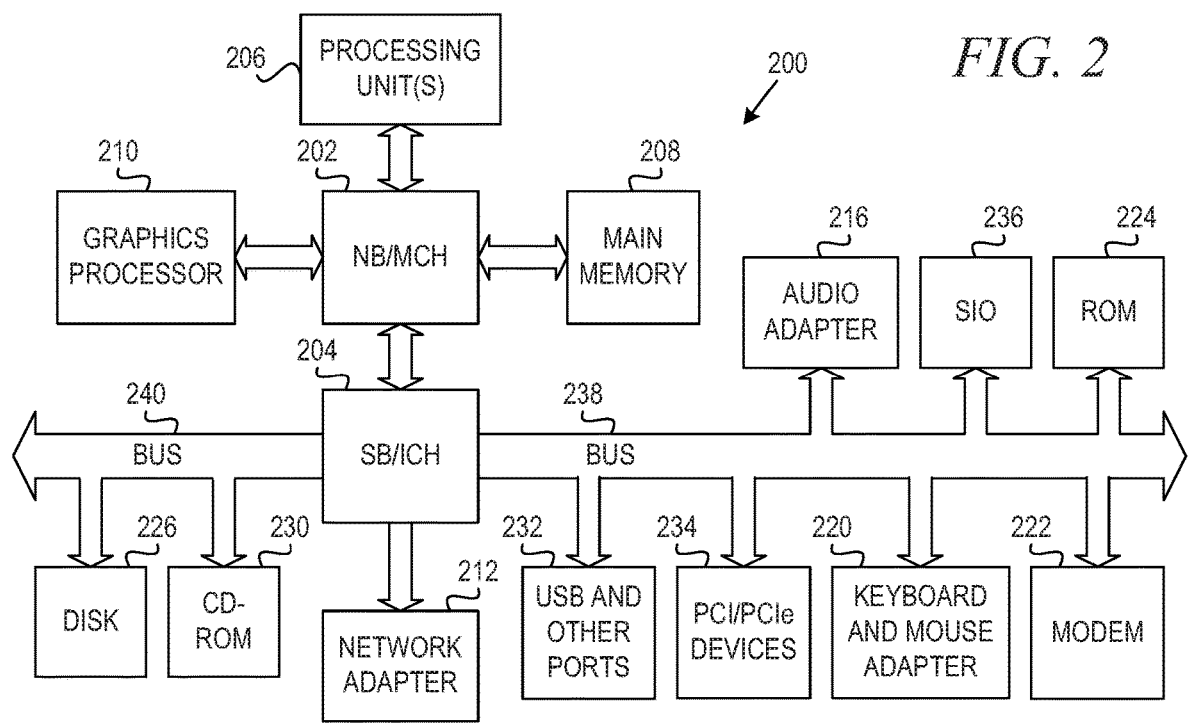
FIG. 2 is a block diagram of an example data processing system in which aspects of the illustrative embodiments are implemented.
Figure 3:
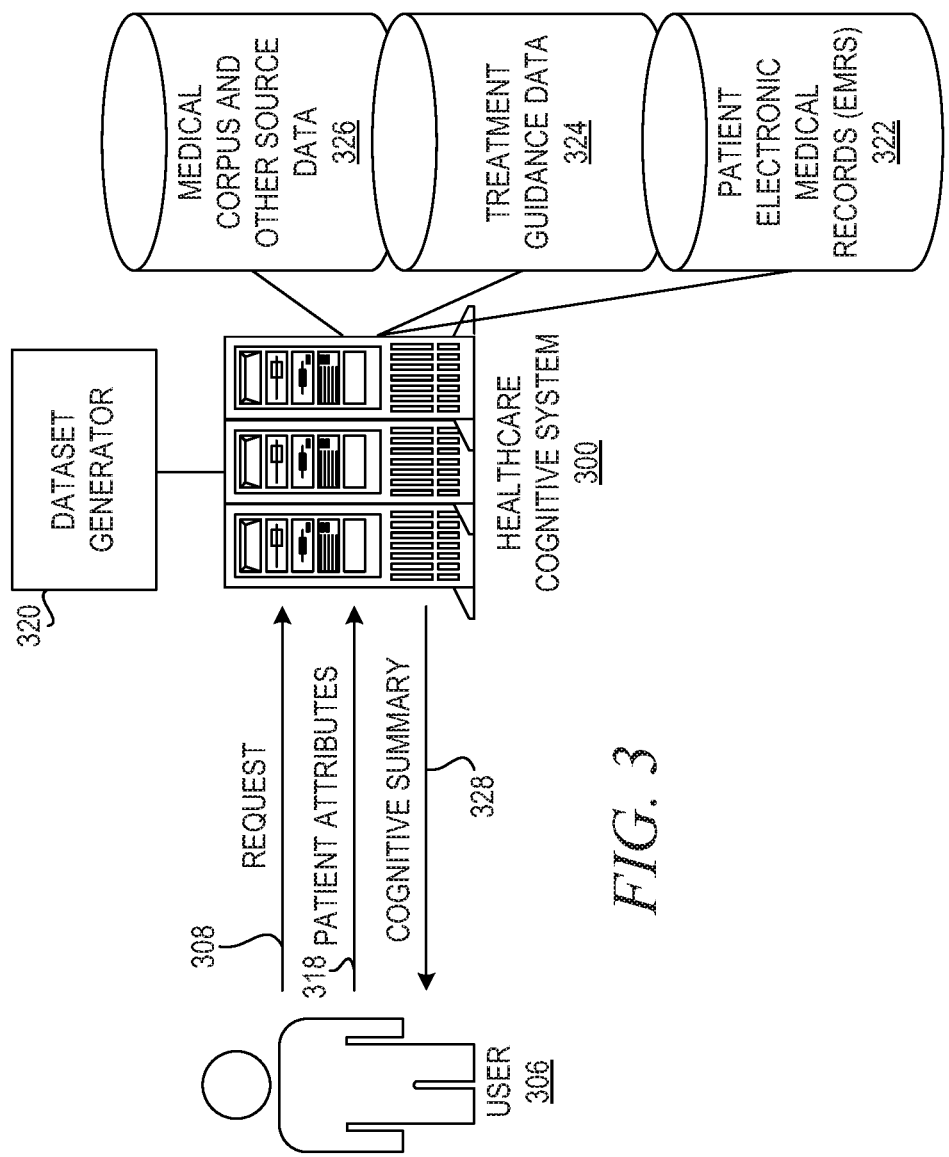
FIG. 3 is an example diagram illustrating an interaction of elements of a healthcare cognitive system in accordance with one illustrative embodiment.

As noted above, the present invention provides mechanisms for generating health care clinical data controlled datasets. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for presenting relevant information using a graphical presentation engine.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for cognitive analysis of EMR data, another request processing pipeline being configured for patient monitoring, etc.

Moreover, each request processing pipeline may have its own associated corpus or corpora that it ingests and operates on, e.g., one corpus for blood disease domain documents and another corpus for cancer diagnostics domain related documents in the above examples. These corpora may include, but are not limited to, EMR data. The cognitive system may use a knockout autoencoder for detecting anomalies in biomedical images.

As will be discussed in greater detail hereafter, the illustrative embodiments may be integrated in, augment, and extend the functionality of these QA pipeline, or request processing pipeline, mechanisms of a healthcare cognitive system with regard to an electronic medical record completeness and data quality assessment mechanism. Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like, and the answer may be returned in a natural language format maximized for efficient comprehension in a point-of-care clinical setting. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108, which comprises a plurality of stages for processing an input question/request based on information obtained from the corpus or corpora of data 106. The pipeline 108 generates answers/responses for the input question or request based on the processing of the input question/request and the corpus or corpora of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process may be repeated for each of the candidate responses to generate a ranked listing of candidate responses, which may then be presented to the user that submitted the input request, e.g., a user of client computing device 110, or from which a final response is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language request, the illustrative embodiments are not limited to such. Rather, the input request may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a dataset generator 120 for capturing and storing relevant statistics and value properties about a client's clinical dataset. The dataset generator 120 captures and stores these statistics from multiple client datasets in order to include data types, data states, and data values that are unique to an individual client dataset or specific to data from a particular data source, e.g., EMR, PMS, etc. Dataset generator 120 applies aggregation algorithms to determine a dataset that includes those data that are unique and those data that are aggregated and loads the result into a single aggregated data map data structure. Dataset generator 120 includes a module that can be directed to create an empty client dataset construct and then populate it with new artificial data that retains the statistics and value properties of the aggregated data map.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements a cognitive system 100 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide a cognitive summary of EMR data for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302, social history, and demographic information about the patient, symptoms, and other pertinent information obtained from responses to questions or information obtained from medical equipment used to monitor or gather data about the condition of the patient. In one embodiment, patient attributes 318 may include identification of a biomedical image for processing to detect anomalies. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a cognitive summary of EMR data 328 to the user 306 to assist the user 306 in treating the patient based on their reported symptoms and other information gathered about the patient. The healthcare cognitive system 300 operates on the request 308 and patient attributes 318 utilizing information gathered from the medical corpus and other source data 326, treatment guidance data 324, and the patient EMRs 322 associated with the patient to generate cognitive summary 328. In one embodiment, patient EMR data 322 may include biomedical images. The cognitive summary 328 may be presented in a ranked ordering with associated supporting evidence, obtained from the patient attributes 318 and data sources 322-326, indicating the reasoning as to why portions of EMR data 322 are being provided. Cognitive summary 328 may also include a marked image that identifies detected anomalies.

In accordance with the illustrative embodiments herein, the healthcare cognitive system 300 is augmented to include a dataset generator 320 for using real patient data in patient EMRs 322, for example, to generate an artificial dataset that resembles the real data. Dataset generator 320 captures and stores statistics from multiple client datasets and applies aggregation algorithms to determine a dataset that includes those data that are unique to those data that are aggregated and loads the result into a single aggregated data map. Dataset generator 320 then creates an empty client dataset construct and populates it with new artificial data that retains the statistics and value properties of the aggregated data map.

Figure 4:
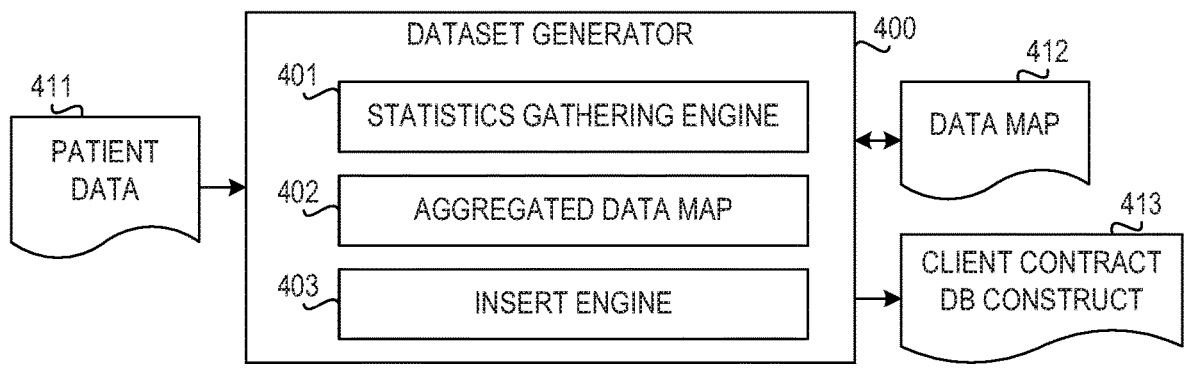
FIG. 4 is a block diagram of a dataset generator in accordance with an illustrative embodiment.

FIG. 4 is a block diagram of a dataset generator in accordance with an illustrative embodiment. The dataset generator 400 comprises a statistics gathering engine 401, an aggregated data map engine 402, and an insert engine 403. Dataset generator 400 receives patient data 411. The statistics gathering engine 401 calculates and stores statistics and metrics across six different data dimensions, as follows:

1. Patient clinical demographics: the demographic values that affect clinical and health care results, including gender, age, and attribution statistics.

2. Patient logical demographics: the demographics that are used to identify and communicate with patients, including social security number, telephone number, email address, etc.

3. Patent clinical events: all coded clinical events whose presence or absence is used to derive clinical health and population health results, including appointments, billing codes, EMR data, etc.

4. Patient communication events: patient communication history statistics.

5. Provider demographics: data about health care providers, their facilities, and their relationships to patients (subscriber, facility, provider, and appointment calendar statistics).

6. Application statistics data: data relevant to products and services that read data from a repository and pass relevant clinical health and population health results to consumers of those results.

The statistics gathering engine 401 is configurable in that as many client datasets as desired to capture a sufficient cross-section will be passed to the engine. When statistics gathering engine 401 is triggered, the engine gathers and stores its results in a client-specific data map 412 for each client involved in the survey. In one embodiment, statistics gathering engine 401 is built inside of the data repository from which the client patient data 411 is stored (e.g., structured query language (SQL)).

In aggregated data map engine 402, an aggregation algorithm uses one of several aggregation types that direct aggregated data map engine 402 to either combine unique values and their strengths of presence (frequency of use across a single dataset, frequency of use across multiple sources, etc.) for each data point, or to average certain data points and sum other data points in order to capture the "ideal" cross-section of client data. The data map 412 is a fluid map that can be iteratively updated using statistics gathering engine 401 so that at any time, a realistic picture of client data is ready to consume.

One approach to deriving an ideal data "shape," particularly with respect to data distributed across a patient population (e.g., age) is to start by ranking the data based on patient counts within different brackets of a particular data type, for example, pediatric patients. Then, as data from multiple sources is evaluated, those ranked values that persist across multiple data sources can be considered a reliably relevant ranking. Those that do not persist can be evaluated for probability of accuracy, and then a likely rank can be derived.

In one embodiment, aggregated data map engine 402 and data map 412 is built inside the data repository from which the client persistent data is stored.

Insert engine 403 consumes the aggregated data map 412 and spools up data to be inserted into a client database construct 413. As used herein, "spooling up data" refers to generating artificial data that resembles the real client data with respect to statistics and value properties. This may also be referred to as "spinning up data." Dataset generator 400 creates an empty database 413 in the target data repository (e.g., SQL). Then, insert engine 403 uses the statistics and metrics in the aggregated data map 412 to inject newly created data built to the specifications defined in the data map 412. Because the insert engine 403 manufactures entirely new data based on how client data looks "in the real world," there is assurance that the data will be agnostic enough to satisfy basic requirements for widely varied de-identified data. Additionally, these spun-up data become a baseline of "expected results" for most regression testing.

Changes to insert engine 403 and changes in industry-driven medical condition and disease state definitions used by software products that consume these definitions can be accounted for with test cases and constructed on an ad hoc basis, but all other engine and data handling behavior that is not touched by targeted development work can be easily validated against the baseline.

Insert engine 403 contains configurable switches and controls that allow a user to dial in the size and level of data output needed. In one example embodiment, insert engine 403 uses t-shirt sizing (extra small (XS), small (S), medium (M), large (L), extra large (XL), etc.) to spin up to a desired size that will also include those components or data dimensions pertinent to a software developer team's scope (clinical rules, communication rules, web page, reporting, etc.).

Figure 5B:
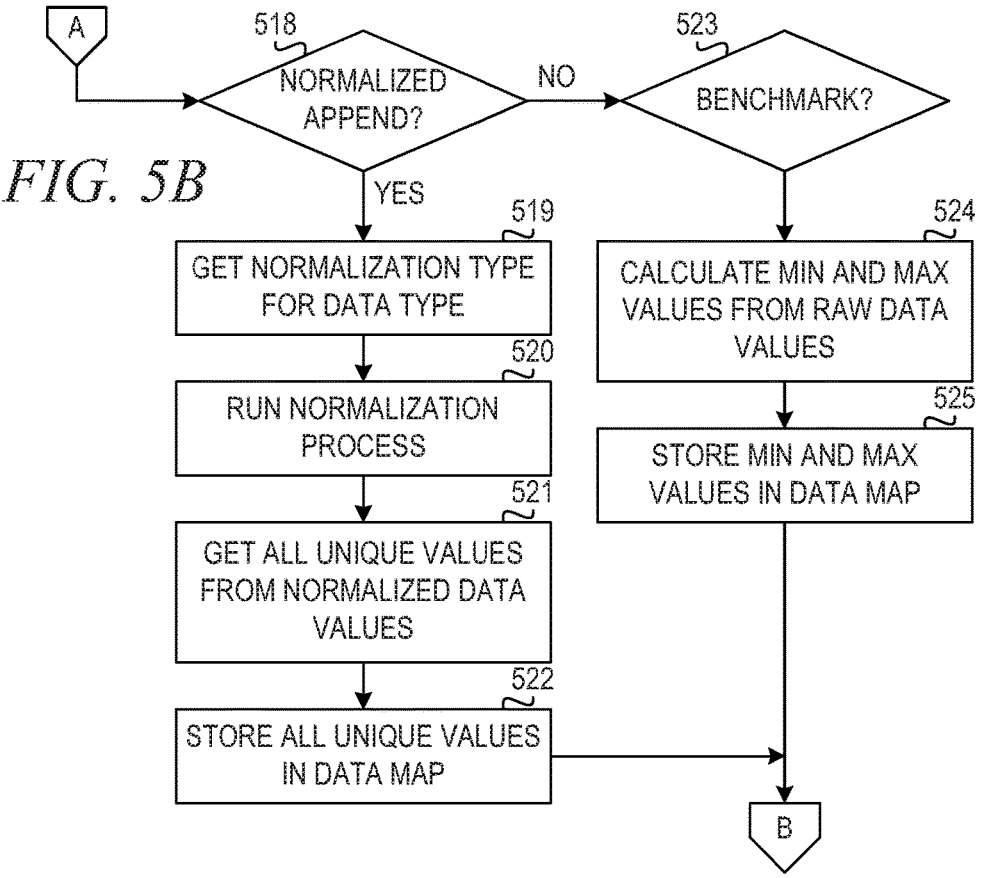
FIGS. 5A and 5B depict a flowchart illustrating operation of a mechanism performing an aggregation process in accordance with an illustrative embodiment.
Figure 5A:
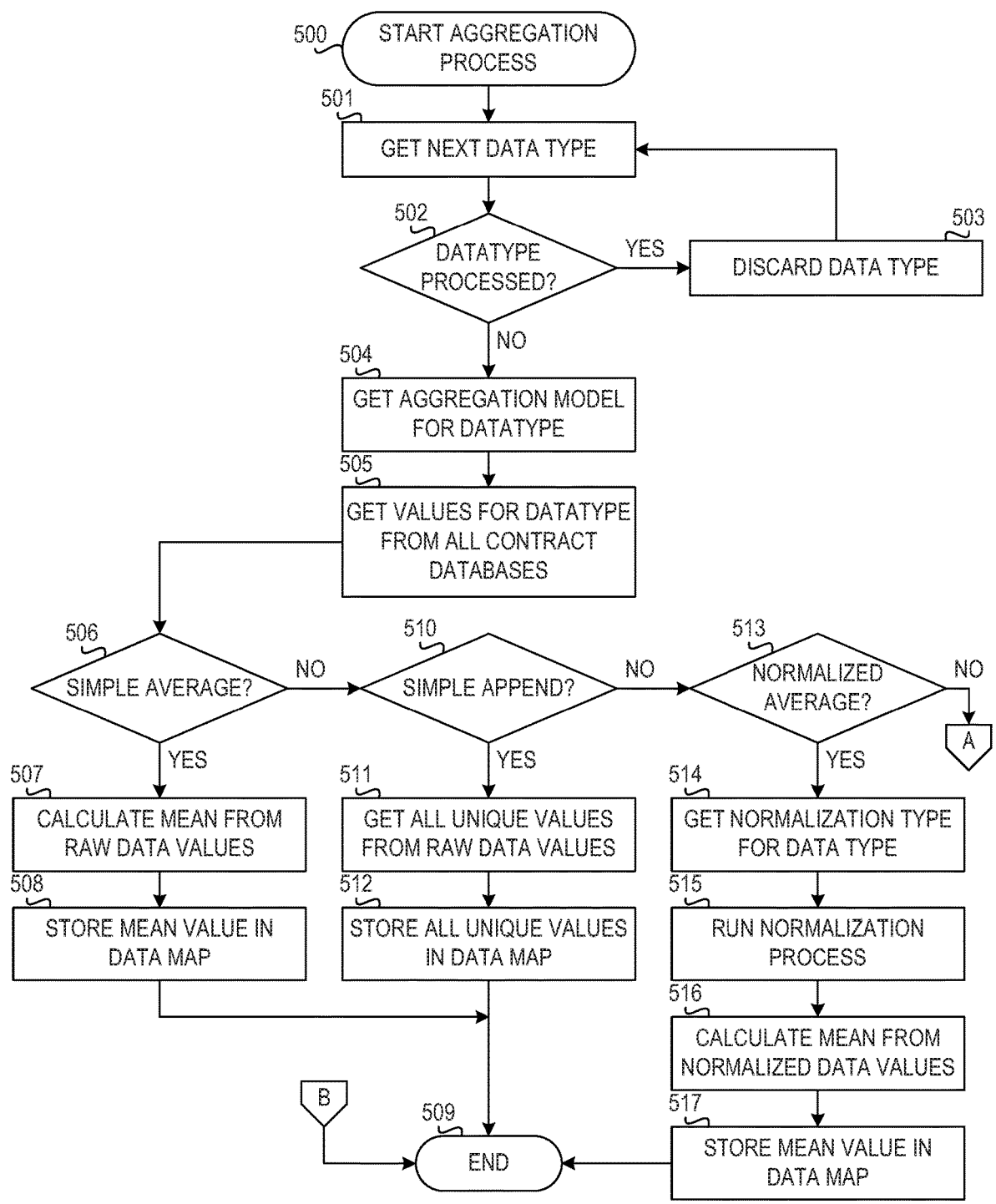

FIGS. 5A and 5B depict a flowchart illustrating operation of a mechanism performing an aggregation process in accordance with an illustrative embodiment. With reference to FIG. 5A, operation begins with the mechanism starting the aggregation process (block 500). The mechanism gets the next data type (block 501). The mechanism determines whether the data type has been processed (block 502). If the data type has been processed, then the mechanism discards the data type (block 503), and operation returns to block 501 to get the next data type.

If the mechanism determines that the data type has not been processed in block 502, then the mechanism gets an aggregation model for the data type (block 504) and gets values for the data type from all contract databases (block 505). The mechanism then determines whether the aggregation model is simple average (block 506). If the aggregation model for the data type is simple average, then the mechanism calculates a mean from the raw data values (block 507) and stores the mean value in the data map (block 508). Thereafter, the aggregation process ends (block 509).

If the mechanism determines that the aggregation model for the data type is not simple average in block 506, then the mechanism determines whether the aggregation model is simple append (block 510). If the aggregation model is simple append, then the mechanism gets all unique values from the raw data values (block 511) and stores all unique values in the data map (block 512). Thereafter, the aggregation process ends (block 509).

If the mechanism determines that the aggregation model for the data type is not simple append in block 510, then the mechanism determines whether the aggregation model is normalized average (block 513). If the aggregation model is normalized average, then the mechanism gets a normalization type for the data type (block 514) and runs a normalization process (block 515). The operation of running a normalization process is described in further detail below with reference to FIGS. 6A-6C. The mechanism then calculates a mean from the normalized data values (block 516) and stores the mean in the data map (block 517). Thereafter, the aggregation process ends (block 509).

If the mechanism determines that the aggregation model for the data type is not normalized average in block 513, then operation proceeds to FIG. 5B, and the mechanism determines whether the aggregation model is normalized append (block 518). If the aggregation model for the data type is normalized append, then the mechanism gets a normalization type for the data type (block 519) and runs a normalization process (block 520). The operation of running a normalization process is described in further detail below with reference to FIGS. 6A-6C. The mechanism then gets all unique values from normalized data values (block 521) and stores all unique values in the data map (block 522). Thereafter, the aggregation process ends (block 509).

If the mechanism determines that the aggregation model for the data type is not normalized append in block 518, then the aggregation model is benchmark (block 523). The mechanism calculates minimum (min) and maximum (max) values from the raw data values (block 524) and stores the min and max values in the data map (block 525). Thereafter, operation returns to block 509 in FIG. 5A, and the aggregation process ends.

Figure 6A:
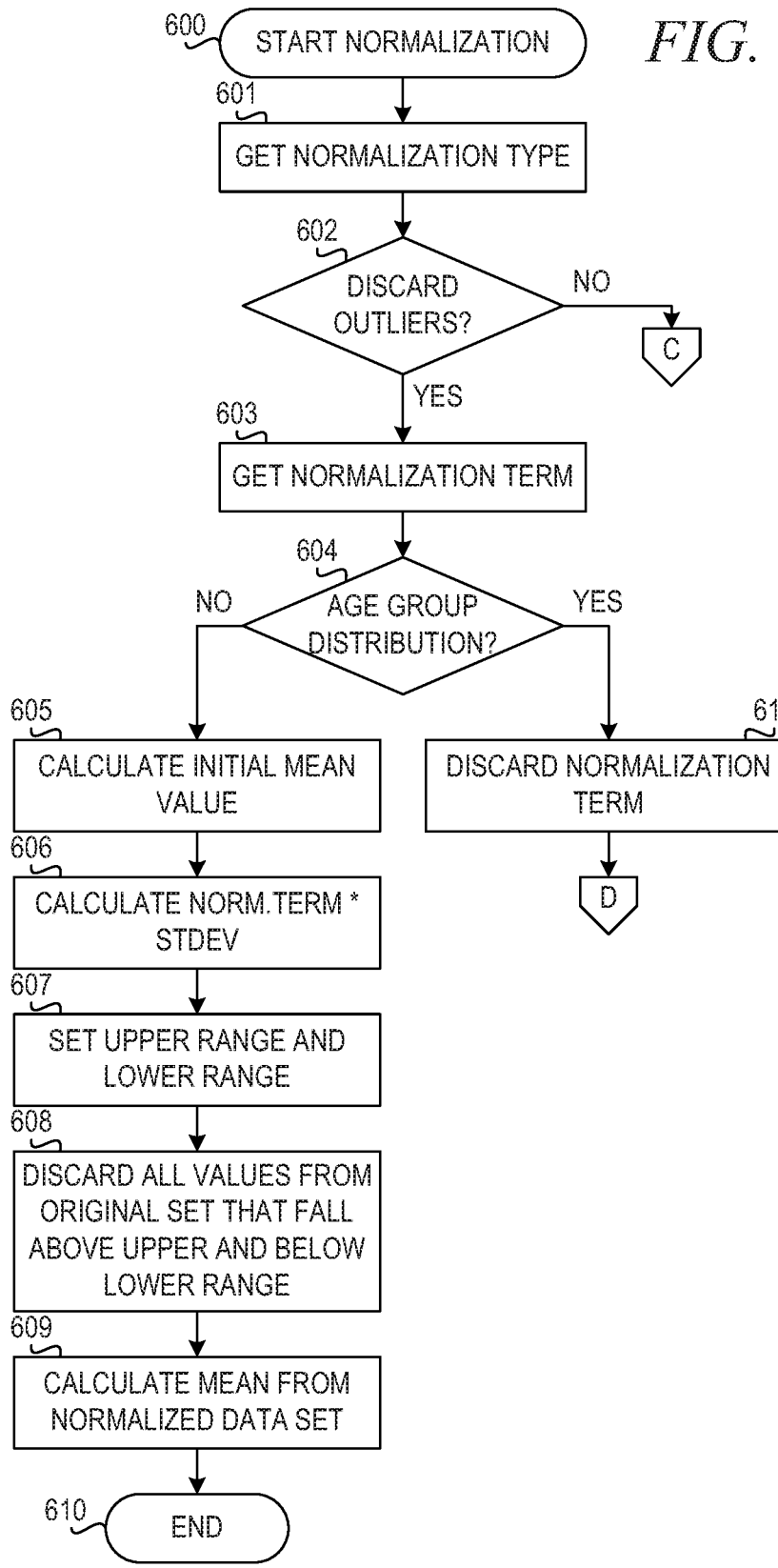
FIGS. 6A-6C depict a flowchart illustrating operation of a mechanism for performing a normalization process in accordance with an illustrative embodiment.
Figure 6B:
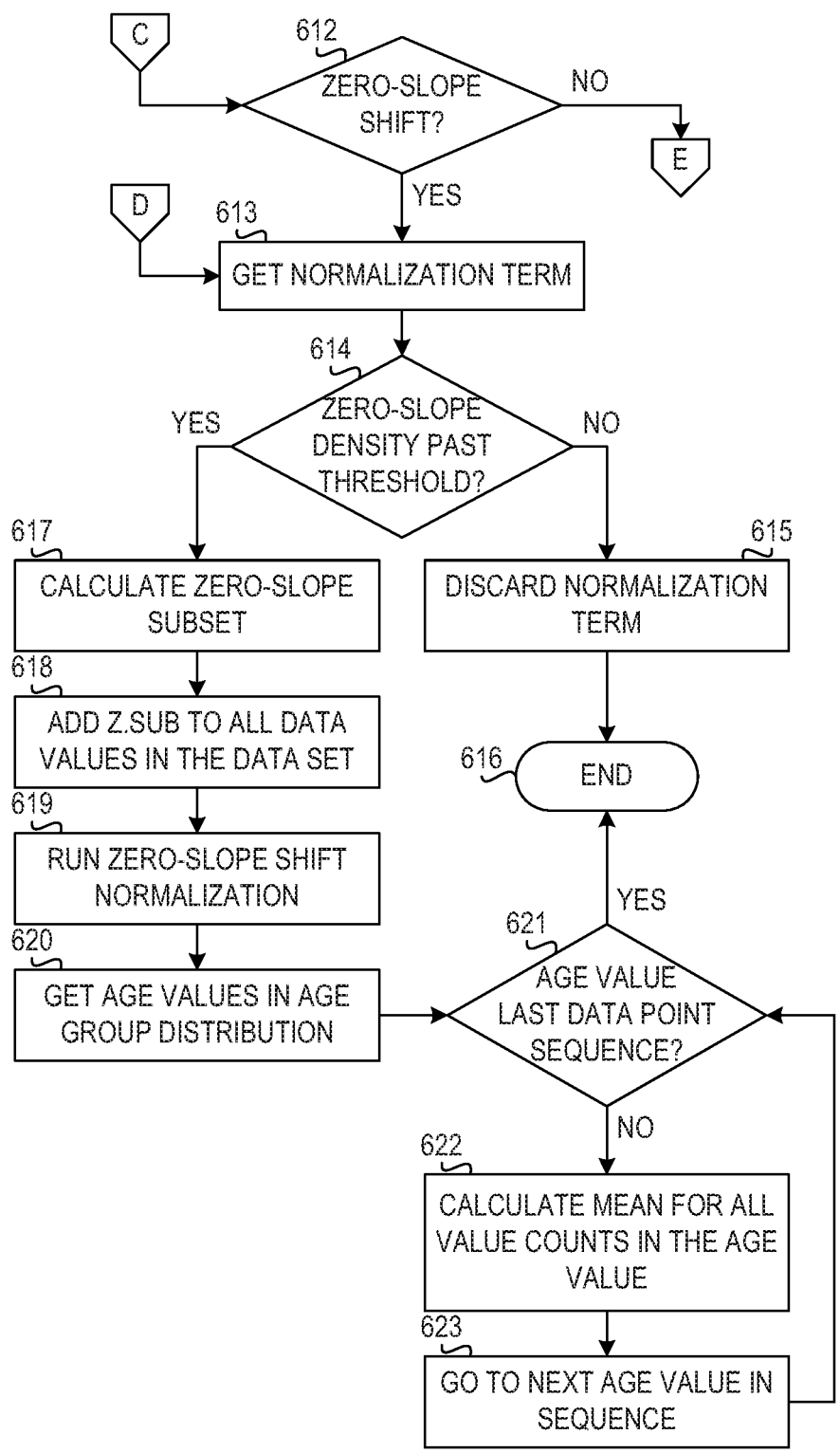
Figure 6C:
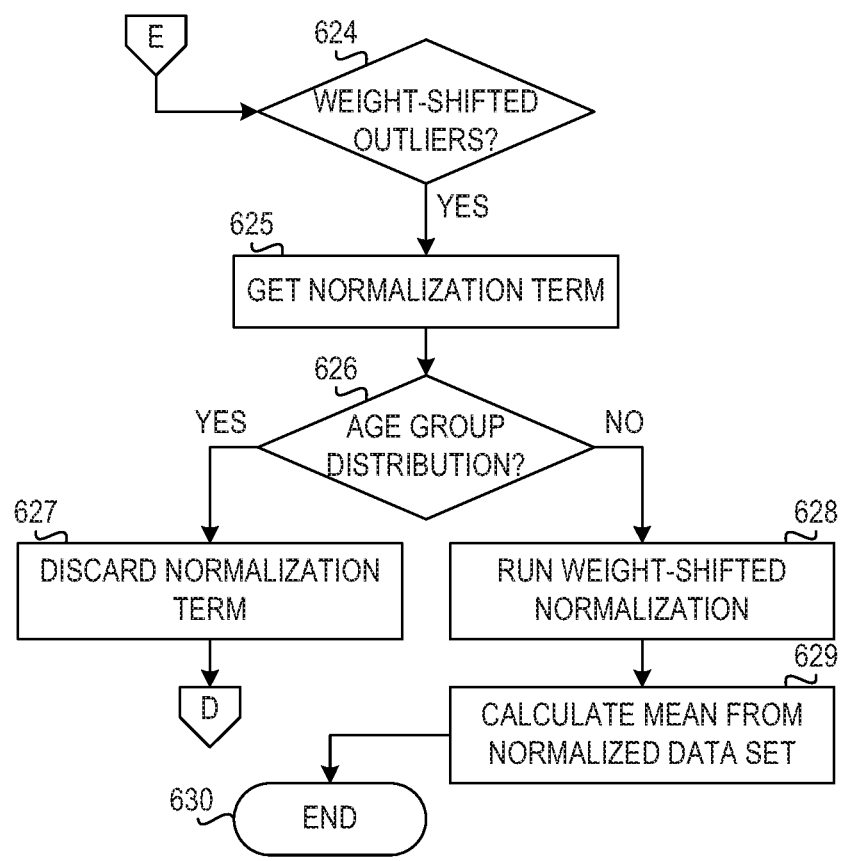

FIGS. 6A-6C depict a flowchart illustrating operation of a mechanism for performing a normalization process in accordance with an illustrative embodiment. With reference to FIG. 6A, operation begins with the mechanism starting the normalization process (block 600). The mechanism gets a normalization type for the data type (block 601). The mechanism determines whether the normalization type is discard outliers (DO) (block 602). If the normalization type is discard outliers, then the mechanism gets the normalization term (NORM.TERM expressed as STDEV threshold) (block 603). The mechanism determines whether there is an age group distribution (block 604). If there is no age group distribution, then the mechanism calculates an initial mean value (IM) (block 605), calculates NORM.TERM*STDEV (block 606). The mechanism then sets the upper range=(IM+(NORM.TERM*STDEV) and sets the lower range=(IM−NORM.TERM*STDEV) (block 607). The mechanism discards all values from the original set that fall above the upper range and below the lower range (block 608). Then, the mechanism calculates the mean from the normalized data set (block 609), and the normalization process ends (block 610).

If there is an age group distribution in block 604, then the mechanism discards the normalization term (block 611). Thereafter, operation proceeds to block 613 in FIG. 6B to be described later.

If the normalization type is not discard outliers in block 602, then operation proceeds to block 612, and the mechanism determines whether the normalization type is zero-slope shift. If the normalization type is zero-slope shift, then the mechanism gets the normalization term (zero-slope density in data set expressed as a percentage) (block 613). The mechanism determines whether the zero-slope density is past a predetermined threshold (block 614). If the zero-slope density is past the threshold, then the mechanism calculates the zero-slope subset by counting the longest number of data points without a slope change (Z.SUB) (block 617). The mechanism adds Z.SUB to all data values in the data set (block 618). The mechanism then runs zero-slope shift normalization (block 619). The operation of zero-slope shift normalization is described in further detail below with reference to FIGS. 8A and 8B. Then, the mechanism gets the age values in the age group distribution (block 620).

Then, the mechanism then determines whether the age value is the last data point in the sequence (block 621). If the age value is the last data point, then the normalization process ends (block 616). If the age value is not the last data point in the sequence in block 621, then the mechanism calculates the mean for all value counts in the age value (block 622) and goes to the next age value in the sequence (block 623). Thereafter, operation returns to block 621 to determine whether the age value is the last data point in the sequence.

Returning to block 614, if the zero-slope density is not past the threshold, then the mechanism discards the normalization term (block 615). Thereafter, the normalization process ends (block 616).

If the normalization type is not zero-slope shift in block 612, then operation proceeds to block 624 in FIG. 6C, and the normalization type is weight-shifted outliers (block 624). The mechanism then gets the normalization term (NORM.TERM expressed as STDEV threshold) (block 625). The mechanism determines whether there is an age group distribution (block 626). If there is an age group distribution, then the mechanism discards the normalization term (block 627). Thereafter, operation returns to block 613 in FIG. 6B. If there is not an age group distribution in block 626, then the mechanism runs weight-shifted normalization (block 628). Operation of the weighted or weight-shifted normalization process is described in further detail with reference to FIG. 7. Then, the mechanism calculates a mean from the normalized data set (block 629), and the normalization process ends (block 630).

Figure 7:
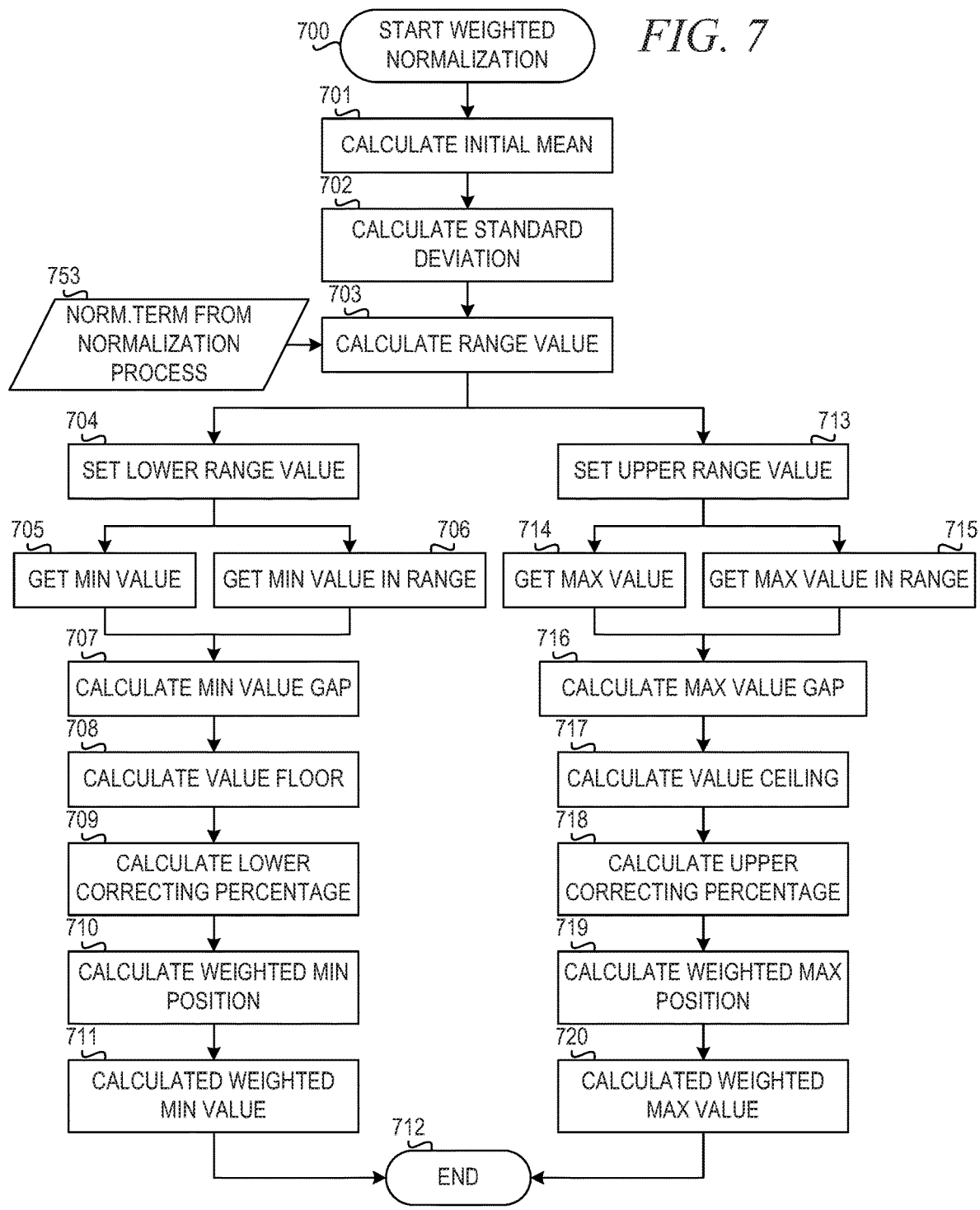
FIG. 7 is a flowchart illustrating operation of a mechanism performing weighted normalization in accordance with an illustrative embodiment.

FIG. 7 is a flowchart illustrating operation of a mechanism performing weighted normalization in accordance with an illustrative embodiment. Operation begins with the mechanism starting a weighted normalization process (block 700). The mechanism calculates the initial mean (IM) (block 701) and calculates the standard deviation (STDEV) (block 702). The mechanism then calculates the range value (RV) from the NORM.TERM from the normalization process 753 (block 703).

The mechanism sets the lower range value (LRV) (bock 704). The mechanism gets the minimum value (MNV) (block 705) and gets the min value in the range (MNVR) (block 706). The mechanism calculates the min value gap (MNVG)=LRV−MNVR (block 707). The mechanism calculates the value floor (VF)=MNVR−MNV (block 708). The mechanism then calculates the lower correcting percentage (LCP)=MNVGNF (block 709). The mechanism then calculates the weighted minimum position (WMNP)=LCP*MNVG (block 710). The mechanism then calculates the weighted minimum value (WMNV)=MNVR−WMNP (block 711). Thereafter, the weighted normalization process ends (bock 712).

The mechanism also sets the upper range value (URV) (block 713). The mechanism gets the maximum value (MXV) (block 714) and the maximum value in range (MXVR) (block 715). The mechanism calculates the maximum value gap (MXVG)=URV−MXVR (block 716). The mechanism then calculates the value ceiling (VC)=MXV−MXVR (block 717). The mechanism then calculates the upper correcting percentage (UCP)=MXVGNC (block 718).

The mechanism then calculates the maximum position (WMXP)=UCP*MXVG (block 719). The mechanism then calculates the weighted maximum value (WMXV)=MXVR+WMXP (block 720). Thereafter, the weighted normalization process ends (block 712).

Figure 8A:
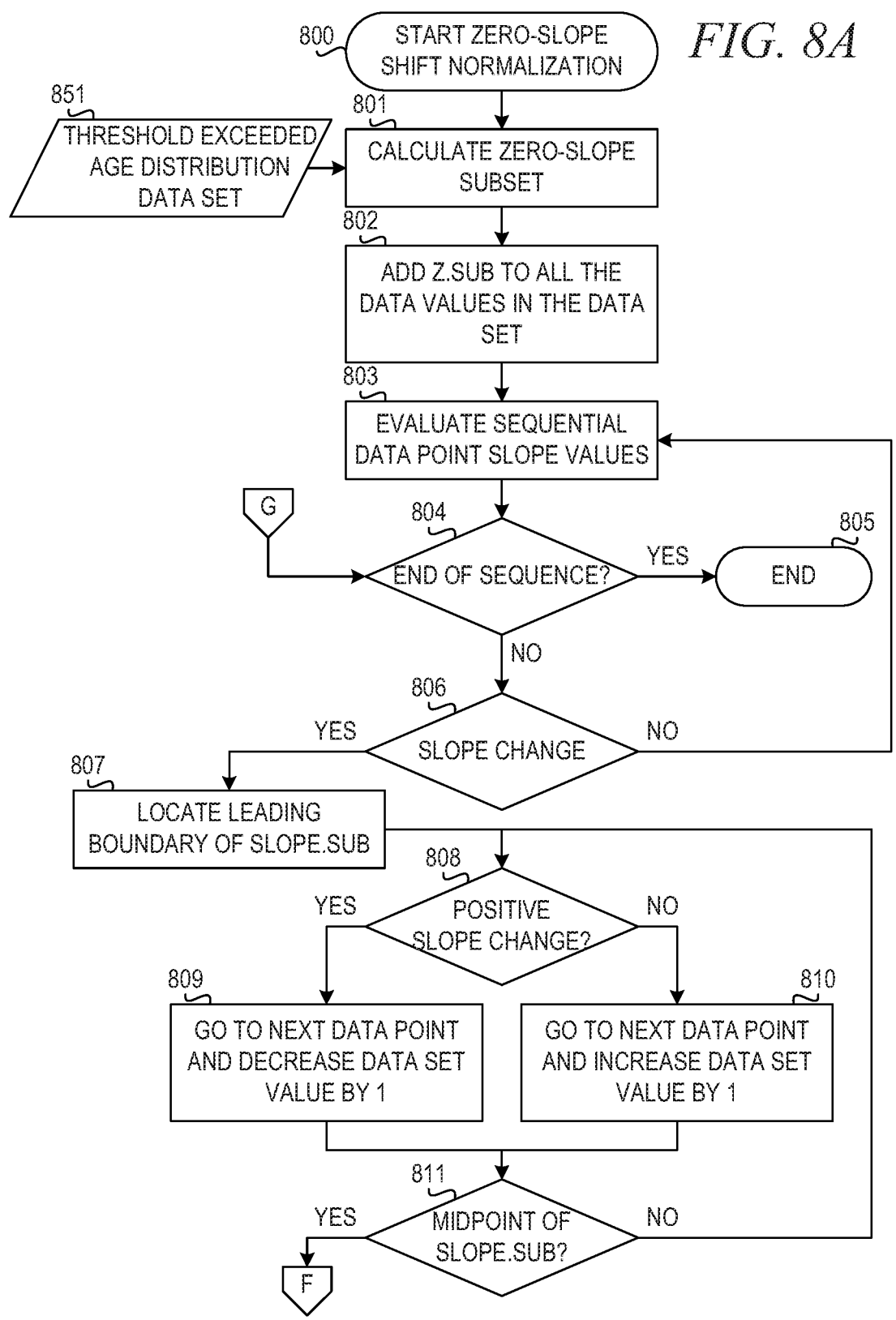
FIGS. 8A and 8B depict a flowchart illustrating operation of mechanism for performing a zero-slope shift normalization process in accordance with an illustrative embodiment.
Figure 8B:
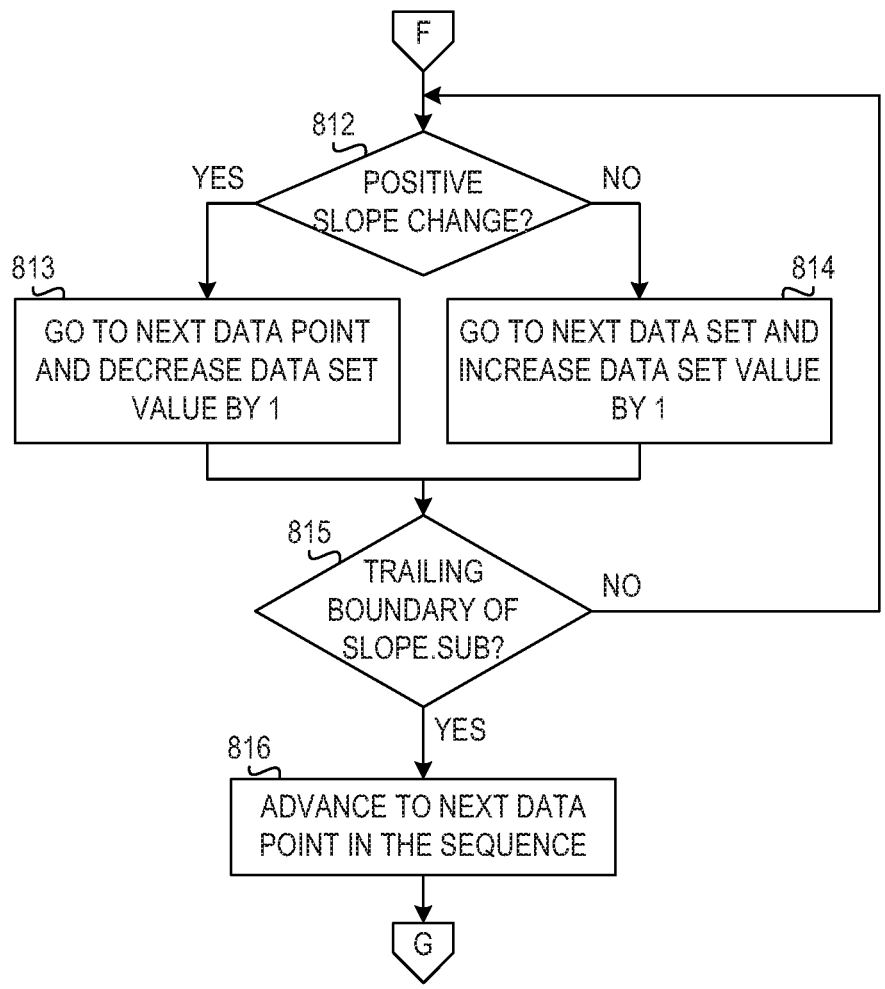

FIGS. 8A and 8B depict a flowchart illustrating operation of mechanism for performing a zero-slope shift normalization process in accordance with an illustrative embodiment. Operation begins with the mechanism starting the zero-slope shift normalization process (block 800). The mechanism calculates the zero-slope subset by counting the longest number of data points without a slope change (Z.SUB) based on the threshold exceeded age-distribution data set 851 (block 801). The mechanism adds Z.SUB to all of the data values in the data set (bock 802) and evaluates the sequential data point slope values (block 803). The mechanism determines whether the end of the sequence is reached (block 804). If the end of the sequence is reached, then the zero-slope shift normalization process ends (block 805).

If the end of the sequence is not reached in block 804, then the mechanism determines whether there is a slope change at the boundary of three or more flat-slope data points (SLOPE.SUB) (block 806). If there is no slope change, then operation returns to block 803 to evaluate the sequential data point slope values.

If there is a slope change in block 806, then the mechanism locates the leading boundary of SLOPE.SUB (block 807). Then, the mechanism determines whether there is a positive slope change (block 808). If there is a positive slope change, then the mechanism goes to the next data point and decreases the data set value by one (block 809). If there is not a positive slope change, then the mechanism goes to the next data point and increases the data set value by one (block 810). The mechanism then determines whether the data point is the midpoint of SLOPE.SUB (block 811). If the data point is not the midpoint of SLOPE.SUB, then operation returns to block 808.

If the data point is the midpoint of SLOPE.SUB in block 811, then operation proceeds to block 812 in FIG. 8B, and the mechanism determines whether the evaluated point after the midpoint has a positive slope change. If the data point after the midpoint has a positive slope change, then the mechanism goes to the next data point and decreases the data set value by one (block 813). If the data point after the midpoint does not have a positive slope change in block 812, then the mechanism goes to the next data set and increases the data set value by one (block 814). Thereafter, the mechanism determines whether the trailing boundary of SLOPE.SUB is reached (block 815). If the trailing boundary is not reached, then operation returns to block 812. If the trailing boundary is reached in block 815, then the mechanism advances to the next data point in the sequence (block 816), and operation returns to block 804 in FIG. 8A.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to specifically configure the processor to implement a data set generator, the method comprising:

calculating, by a statistics gathering engine executing within the data set generator, statistics and metrics across multiple data dimensions for a plurality of clients and a plurality of each client's data sources, wherein the multiple data dimensions comprise patient clinical demographics comprising demographic values that affect clinical and health care results, patient logical demographics that are used to identify and communicate with patients, patient clinical events, patient engagement events comprising coded clinical events whose presence or absence is used to derive clinical health and population health results, patient communication history statistics, provider demographics comprising data about health care providers, their facilities, and their relationships to patients, and application end user and usage statistics data comprising data relevant to products and services that read data from a repository and pass relevant clinical health and population health results to consumers of those results;

storing, by the statistics gathering engine, the statistics and metrics in a client-specific data map data structure for each client;

aggregating, by an aggregated data map engine executing within the data set generator, the statistics and metrics into an aggregated data map, wherein aggregating the statistics and metrics comprises for a given data type, determining an aggregation model for the given data type, obtaining raw data values for the given data type from all client-specific data map data structures, and aggregating the raw data values for the given data type based on the aggregation model;

storing, by the aggregated data map engine, the aggregated data map in an aggregated data map data structure;

creating, by the data set generator, a client database construct; and populating, by an insert engine executing within the data set generator, the client database construct with new data based on the aggregated data map data structure.

2. The method of claim 1, wherein aggregating the statistics and metrics further comprises:

responsive to the aggregation model being simple average, calculating a mean value from the raw data values and storing the mean value in the aggregated data map data structure.

3. The method of claim 1, wherein aggregating the statistics and metrics further comprises:

responsive to the aggregation model being simple append, getting all unique values from the raw data values and storing the unique values in the aggregated data map data structure.

4. The method of claim 1, wherein aggregating the statistics and metrics further comprises:

responsive to the aggregation model being normalized average:
  determining a normalization type for the given data type;
  performing a normalization process based on the normalization type to form normalized data values;
  calculating a mean value from the normalized data values; and
  storing the mean value in the aggregated data map data structure.

5. The method of claim 4, wherein the normalization type comprises discard outliers, zero-slope shift, or weight-shifted outliers.

6. The method of claim 1, wherein aggregating the statistics and metrics further comprises:

responsive to the aggregation model being normalized append:
  determining a normalization type for the given data type;
  performing a normalization process based on the normalization type to form normalized data values;
  getting all unique values from the normalized data values; and
  storing the unique values in the aggregated data map data structure.

7. The method of claim 6, wherein the normalization type comprises discard outliers, zero-slope shift, or weight-shifted outliers.

8. The method of claim 1, wherein aggregating the statistics and metrics further comprises:

responsive to the aggregation model being benchmark, calculating minimum and maximum values from the raw data values and storing the minimum and maximum values in the aggregated data map data structure.

9. The method of claim 4, wherein performing the normalization process comprises:

responsive to the normalization type being discard outliers, determining a normalization term and a standardized deviation;

determining whether there is an age group distribution;

responsive to there being no age group distribution, calculating an initial mean value based on the normalization term and the standardized deviation;

setting an upper range and a lower range; and discarding all values from the original set that fall above the upper range and below the lower range.

10. The method of claim 4, wherein performing the normalization process comprises:

responsive to the normalization type being zero-slope shift, determining a normalization term;

responsive to the zero-slope density being past a predetermined threshold, calculating a zero-slope subset by counting a longest number of data points without a slope change, adding the slope change to all data values in the data set, running a zero-slope shift normalization, and determining age values in an age group distribution; and responsive to the age value not being the last data point, calculating a mean for all value counts in each age value.

11. The method of claim 4, wherein performing the normalization process comprises:

responsive to the normalization type being weight-shifted outliers, determining a normalization term;

responsive to there not being an age group distribution, running a weight-shifted normalization and calculating a mean from the normalized data set.

12. A computer program product comprising a non-transitory computer readable medium having a computer readable program stored therein, wherein the computer readable program, when executed on a computing device, causes the computing device to implement a data set generator, wherein the computer readable program causes the computing device to:

calculate, by a statistics gathering engine executing within the data set generator, statistics and metrics across multiple data dimensions for a plurality of clients and a plurality of each client's data sources, wherein the multiple data dimensions comprise patient clinical demographics comprising demographic values that affect clinical and health care results, patient logical demographics that are used to identify and communicate with patients, patient clinical events, patient engagement events comprising coded clinical events whose presence or absence is used to derive clinical health and population health results, patient communication history statistics, provider demographics comprising data about health care providers, their facilities, and their relationships to patients, and application end user and usage statistics data comprising data relevant to products and services that read data from a repository and pass relevant clinical health and population health results to consumers of those results;

store, by the statistics gathering engine, the statistics and metrics in a client-specific data map data structure for each client;

aggregate, by an aggregated data map engine executing within the data set generator, the statistics and metrics into an aggregated data map, wherein aggregating the statistics and metrics comprises for a given data type, determining an aggregation model for the given data type, obtaining raw data values for the given data type from all client-specific data map data structures, and aggregating the raw data values for the given data type based on the aggregation model;

store, by the aggregated data map engine, the aggregated data map in an aggregated data map data structure;

create, by the data set generator, a client database construct; and populate, by an insert engine executing within the data set generator, the client database construct with new data based on the aggregated data map data structure.

13. The computer program product of claim 12, wherein aggregating the statistics and metrics further comprises:
responsive to the aggregation model being simple average, calculating a mean value from the raw data values and storing the mean value in the aggregated data map data structure.

14. The computer program product of claim 12, wherein aggregating the statistics and metrics further comprises:
responsive to the aggregation model being simple append, getting all unique values from the raw data values and storing the unique values in the aggregated data map data structure.

15. The computer program product of claim 12, wherein aggregating the statistics and metrics further comprises:
responsive to the aggregation model being normalized average:
determining a normalization type for the given data type;
performing a normalization process based on the normalization type to form normalized data values;
calculating a mean value from the normalized data values; and
storing the mean value in the aggregated data map data structure.

16. The computer program product of claim 15, wherein the normalization type comprises discard outliers, zero-slope shift, or weight-shifted outliers.

17. The computer program product of claim 12, wherein aggregating the statistics and metrics further comprises:
responsive to the aggregation model being normalized append:
determining a normalization type for the given data type;
performing a normalization process based on the normalization type to form normalized data values;
getting all unique values from the normalized data values; and
storing the unique values in the aggregated data map data structure.

18. The computer program product of claim 17, wherein the normalization type comprises discard outliers, zero-slope shift, or weight-shifted outliers.

19. The computer program product of claim 12, wherein aggregating the statistics and metrics further comprises:
responsive to the aggregation model being benchmark, calculating minimum and maximum values from the raw data values and storing the minimum and maximum values in the aggregated data map data structure.

20. An apparatus, comprising:
a processor; and
a memory coupled to the processor, wherein the memory comprises instructions which, when executed by the processor, cause the processor to implement a data set generator, wherein the instructions cause the processor to:
calculate, by a statistics gathering engine executing within the data set generator, statistics and metrics across multiple data dimensions for a plurality of clients and a plurality of each client's data sources, wherein the multiple data dimensions comprise patient clinical demographics comprising demographic values that affect clinical and health care results, patient logical demographics that are used to identify and communicate with patients, patient clinical events, patient engagement events comprising coded clinical events whose presence or absence is used to derive clinical health and population health results, patient communication history statistics, provider demographics comprising data about health care providers, their facilities, and their relationships to patients, and application end user and usage statistics data comprising data relevant to products and services that read data from a repository and pass relevant clinical health and population health results to consumers of those results;

store, by the statistics gathering engine, the statistics and metrics in a client-specific data map data structure for each client;

aggregate, by an aggregated data map engine executing within the data set generator, the statistics and metrics into an aggregated data map, wherein aggregating the statistics and metrics comprises for a given data type, determining an aggregation model for the given data type, obtaining raw data values for the given data type from all client-specific data map data structures, and aggregating the raw data values for the given data type based on the aggregation model;

store, by the aggregated data map engine, the aggregated data map in an aggregated data map data structure;

create, by the data set generator, a client database construct; and populate, by an insert engine executing within the data set generator, the client database construct with new data based on the aggregated data map data structure.

* * * * *